United States Patent [19]

Lubisch et al.

[11] Patent Number: 5,296,485
[45] Date of Patent: Mar. 22, 1994

[54] SUBSTITUTED N-PHENYLPIPERIDINES AND DRUGS THEREFROM

[75] Inventors: Wilfried Lubisch, Mannheim; Sabine Schult, Heidelberg; Berthold Behl, Ludwigshafen; Michael Kirchengast, Mannheim, all of Fed. Rep. of Germany

[73] Assignee: BASF Aktiengesellschaft, Ludwigshafen, Fed. Rep. of Germany

[21] Appl. No.: 849,250

[22] Filed: Mar. 11, 1992

[30] Foreign Application Priority Data

Mar. 31, 1991 [DE] Fed. Rep. of Germany ....... 4117904

[51] Int. Cl.$^5$ ................. A61K 31/445; C07D 401/04; C07D 217/00
[52] U.S. Cl. .................................... 514/316; 514/183; 514/255; 514/307; 514/317; 514/318; 544/1; 544/360; 546/150; 546/191; 546/194; 546/217; 546/223; 546/229; 546/237
[58] Field of Search ............... 546/193, 194, 217, 191, 546/237, 223, 229, 186, 150; 544/360, 1; 514/255, 307, 316, 317, 318, 183

[56] References Cited

U.S. PATENT DOCUMENTS

| | | | |
|---|---|---|---|
| 3,468,892 | 9/1969 | Tomchecik | 546/208 |
| 4,603,138 | 7/1986 | Maschler | 546/223 |
| 4,603,138 | 7/1986 | Maschler | 514/329 |
| 4,902,800 | 2/1990 | Skotnieki | 546/229 |
| 5,071,859 | 12/1991 | Knudsen | 546/227 |

FOREIGN PATENT DOCUMENTS

M749887 3/1944 Fed. Rep. of Germany .

OTHER PUBLICATIONS

Pang K. S. "Drug Absorption, Distribution and Elimination" p. 89 (1990).
Chem. Ber. 74 (1941) 1648, 1658 and 1661.
Helv. Chim. Acta 26 (1943) 1132.

Primary Examiner—C. Warren Ivy
Assistant Examiner—Celia Chang

Attorney, Agent, or Firm—Keil & Weinkauf

[57] ABSTRACT

Substituted N-phenylpiperidines I

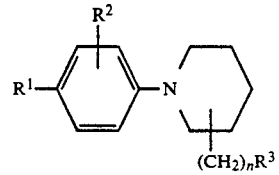

($R^1$=H, $NO_2$, CN, halogen, $C_1$-$C_4$-alkyl, $CF_3$, $OCF_3$, OH, $CH_2OH$, COOH, CHO, NH—CHO, $NH_2$, CO—$NH_2$, 5-tetrazinyl, $R^4$—O—, $R^4$—O—$CH_2$—, $R^4$O—CO—, $R^4$—CO—, $R^4$—NH—CO, $R^4$—CO—NH—, $R^4$—$SO_2$—NH—;

$R^2$=H, $NO_2$, halogen, $C_1$-$C_4$-alkyl or $R^4$—O—;

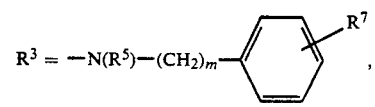

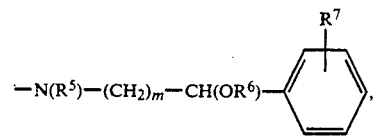

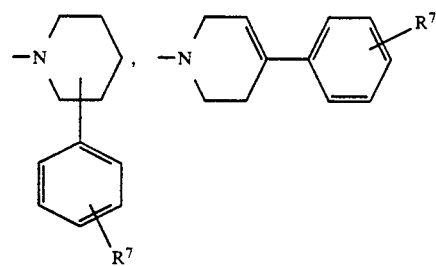

(Abstract continued on next page.)

-continued
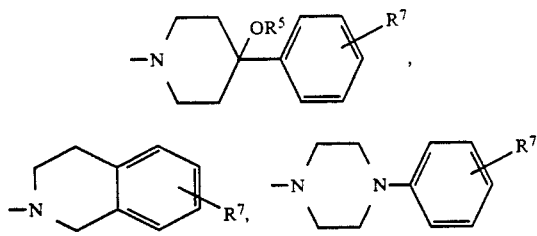
$R^4$ = $C_1$–$C_4$-alkyl or phenyl which can carry one of the $R^2$ radicals;
$R^5$, $R^6$ = H or one of the $R^4$ radicals; $R^7$ = one of the $R^1$ radicals;
n = 0 or 1; m = 1 or 2; with the proviso that $R^3$ is
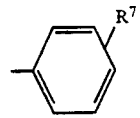
only when n is 1,
and the optical isomers in the case of optical isomerism, and the physiologically tolerated acid addition salts, are suitable as drugs.
3 Claims, No Drawings

SUBSTITUTED N-PHENYLPIPERIDINES AND DRUGS THEREFROM

The present invention relates to N-phenylpiperidines of the formula I

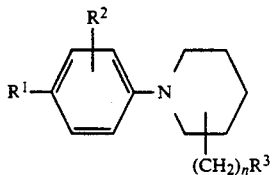

where
R$^1$ is hydrogen, nitro, cyano, halogen, C$_1$–C$_4$-alkyl, trifluoromethyl, trifluoromethoxy, hydroxyl, hydroxymethyl, hydroxycarbonyl, formyl, formylamino, amino, aminocarbonyl, 5-tetrazinyl, R$^4$—O—, R$^4$—O—CH$_2$—, R$^4$—O—CO—, R$^4$—CO—, R$^4$—NH—CO, R$^4$—CO—NH—, R$^4$—SO$_2$—NH—;

R$^2$ is hydrogen, nitro, halogen, C$_1$–C$_4$-alkyl or R$^4$—O—;

R$^3$ is one of the following:

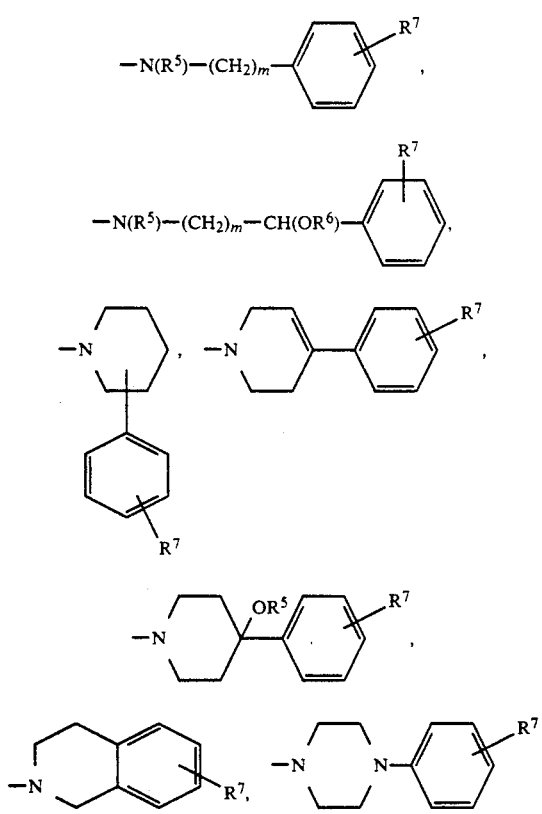

R$^4$ is C$_1$–C$_4$-alkyl or phenyl which may carry one of the R$^2$ radicals;
R$^5$ and R$^6$ are each hydrogen, C$_1$–C$_4$-alkyl or phenyl which can carry one of the R$^2$ radicals;
R$^7$ is one of the R$^1$ radicals
n is 0 or 1;
m is 1 or 2;
with the proviso that R$^3$ can be

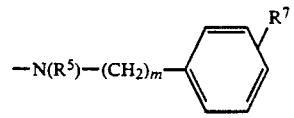

only when n is 1,
and the optical isomers when there is optical isomerism, and the physiologically tolerated acid addition salts.

The present invention also relates to the compounds I for use in pharmaceuticals, to drugs containing the compounds I, and to the use of the compounds I and the salts thereof with physiologically tolerated acids for the production of drugs, especially for the treatment of cardiac arrhythmias.

Drugs for the treatment of cardiac arrhythmias (antiarrhythmics) are, according to Vaughan-Williams [cf. J. Clin. Pharmacol. 24 (1984) 129 and E. M. Vaughan-Williams Ed., Handbook of Exp. Pharmacol. 89, Chapter 2 (1989) ], divided on the basis of their mode of action into four classes:

(I) Sodium antagonists
(II) Adrenergic beta-receptor blockers
(III) Repolarization inhibitors and
(IV) Calcium antagonists.

The antiarrhythmics used to date, most of which belong to class I, can be used only in a narrow therapeutic dose range.

Class III antiarrhythmics are desirable because they normally have fewer side effects than class I antiarrhythmics and, moreover, act on cardiac arrhythmias, especially reentry arrhythmias (recurrent ventricular tachycardia and fibrillation), which cannot be satisfactorily treated with representatives of the other classes. Examples of class III agents are amiodarone [2-butyl-3-benzofuranyl 4-(2-diethylaminoethoxy)-3,5-diiodophenyl ketone; cf. Circulation 68 (1983) 88] and D-sotalol [4'-(1-hydroxy-2-(isopropylamino)ethyl)methanesulfonanilide; cf. Am. Heart. J. 109 (1985) 949 and J. Clin. Pharmacaol. 27 (1987) 708].

Amino-substituted N-phenylpiperidines of the type of compounds I are disclosed in the following publications:

BE-A 678 063 (antiproteolytic action),
EP-A 97 000 (antiarrhythmic action),
U.S. Pat. No. 4,902,800 (as interleukin-I inhibitors).

Other N-phenylpiperidines of the type of compounds I, but which have an antihistamine action, are disclosed in DRP 749 887 (1941), Chem. Ber. 74 (1941) 1648, 1658 and 1661 and Helv. Chim. Acta 26 (1943) 1132.

It is an object of the present invention to provide novel and highly effective antiarrhythmics which act as repolarization inhibitors.

We have found that this object is achieved by the substituted N-phenylpiperidines defined in the first paragraph.

We have also found the use of the compounds I as pharmaceuticals, drugs containing the compounds I, and the use of the compounds I for producing drugs.

Besides their action as antiarrhythmics, we have found that the substituted N-phenylpiperidines I have an affinity for the sigma receptor, for which reason they can also be used as antipsychotics, anticonvulsants, anxiolytics and neuroprotectives.

Substances which bind to sigma receptors (e.g. cyclazocine, pentazocine, ketamine) have psychotomimetic effects in humans [J. Pharmacol. Exp. Ther. 197

(1976) 517]. On the other hand, antipsychotics such as haloperidol and BMY 14802 [α-(4-fluorophenyl)-4-(5-fluoro-2-pyrimidinyl)-1-piperazinebutanol] have a high affinity for sigma binding sites [J. Pharmacol. Exp. Ther. 238 (1986) 739]. In addition, the presence of a relatively large number of sigma receptors in the substantia nigra compacta indicates possible linkage of these receptors to the dopaminergic neurotransmitter system [J. Neurosci. 9 (1989) 326]. The occurrence of the sigma binding sites in other regions of the brain and the high density in other organs such as the spleen, renal cortex, liver and lymphocytes [Endocrinology 124 (1989) 1160 and Pharmacol. 23 (1983) 619] also suggest, however, wide physiological significance of the sigma receptor. It can therefore be expected that sigma ligands will have therapeutic applicability in a large number of pathophysiological processes.

The sigma ligands we have developed are suitable not only as antipsychotics but also as anticonvulsants (spasmolytics), anxiolytics (anxiety-relieving substances) and cytoprotectives in cases of ischemia.

With a view to the intended use of the substituted N-phenylpiperidines I as antiarrhythmics, antipsychotics, anticonvulsants, anxiolytics and neuroprotectives, suitable and preferred substituents are the following:

$R^1$ hydrogen, nitro, cyano; halogen such as fluorine, chlorine, bromine and iodine, especially fluorine, chlorine and bromine; branched or unbranched $C_1$-$C_4$-alkyl such as methyl, ethyl, n-propyl, 1-methylethyl, n-butyl, 1-methylpropyl, 2-methylpropyl and 1,1-dimethylethyl, especially methyl and ethyl; trifluoromethyl, trifluoromethoxy, hydroxyl, hydroxymethyl, hydroxycarbonyl, formyl, formylamino, amino, aminocarbonyl, 5-tetrazinyl; $R^4$—O—, $R^4$—O—$CH_2$—, $R^4$—O—CO—, $R^4$—CO—, $R^4$—NH—CO, $R^4$—CO—NH—, $R^4$—$SO_2$—NH—; $R^1$ is preferably nitro, cyano, halogen, amino and $R^4$—$SO_2$—NH—;

$R^2$ hydrogen, nitro or $R^4$—O—; halogen as mentioned above, especially fluorine and chlorine; branched or unbranched $C_1$-$C_4$-alkyl as mentioned above, especially methyl and ethyl; hydrogen is particularly preferred;

$R^3$ one of the following:

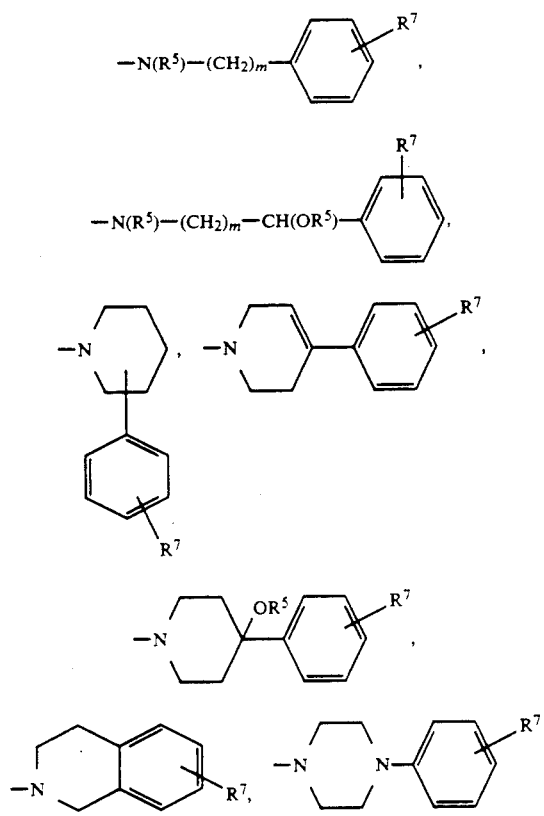

$R^4$ branched or unbranched $C_1$-$C_4$-alkyl as mentioned above, especially methyl and ethyl; phenyl which can also carry one of the $R^2$ radicals;

$R^5$ and $R^6$ hydrogen or one of the $R^4$ radicals;

$R^7$ on of the $R^1$ radicals.

The substituted N-phenylpiperidines I can be obtained in a variety of ways, preferably by one of the following processes:

Process A)

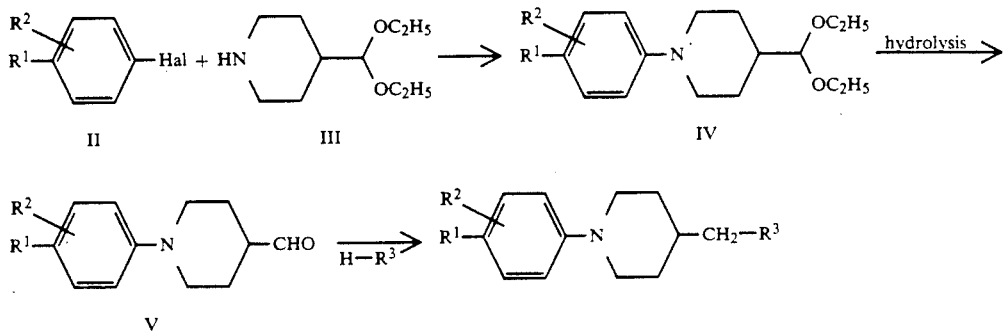

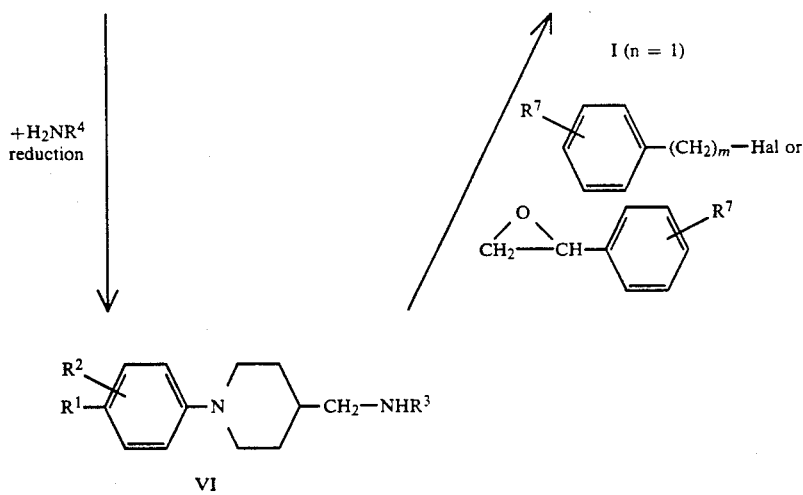

Hal = fluorine, chlorine or bromine

In the first stage, an aryl halide II is reacted with a piperidine III to give a phenylpiperidine IV.

When the aryl halides II carry an electron-attracting substituent $R^1$, for example nitro, cyano, formyl, hydroxycarbonyl or $R^4$—O—CO—, it is advisable to carry out the reaction in a polar solvent such as dimethylformamide, lower alcohols, e.g. methanol or ethanol, or ketones, e.g. acetone. The presence of a base such as potassium carbonate is particularly preferred in this case. The reaction is generally carried out at from 60° to 150° C.

When the aryl halides II do not have an electron-attracting substituent $R^1$ it is advisable to carry out the reaction in the absence of a solvent or in a solvent such a water or a glycol.

A catalytic amount of a metal or metal salt, with copper being particularly preferred as metal component, is generally present in this case. The reaction is normally carried out at from 100° C. to the boiling point of the solvent.

The resulting phenylpiperidine IV is subsequently converted into the aldehyde V by acid hydrolysis, in general by using aqueous acids, preferably aqueous hydrochloric or sulfuric acid. Reductive amination with amines $R^3H$ subsequently results in the compounds I according to the invention. The reductive amination is generally carried out at from 5° to 80° C., preferably 10° to 30° C., in the presence of reducing agents such as sodium cyanoborohydride or hydrogen in the presence of hydrogenation catalysts such as Pd/carbon, Pt/carbon or Raney nickel, expediently in polar organic solvents such as alcohols or dimethylformamide.

Alternatively, the compounds I can be obtained by converting the aldehyde V by reductive amination with an amine $H_2NR^5$, expediently under the conditions described above, into the amine VI, which is subsequently converted by alkylation with a halide

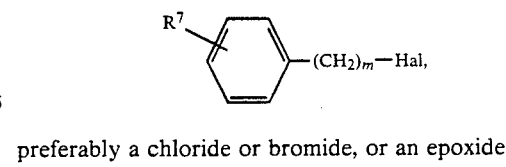

preferably a chloride or bromide, or an epoxide

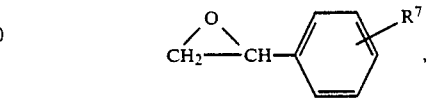

into the compounds I according to the invention.

These reactions are expediently carried out in polar organic solvents, for example in an alcohol or in dimethylformamide, with or without the addition of bases, e.g. alkali metal hydroxides or carbonates such as NaOH, KOH, $Na_2CO_3$ and $K_2CO_3$. The reaction is generally carried out at from 20° to 150° C.

The reaction is advantageously carried out under atmospheric pressure or the autogenous pressure of the solvent; a higher or lower pressure is also possible but normally has no advantages.

Process b)

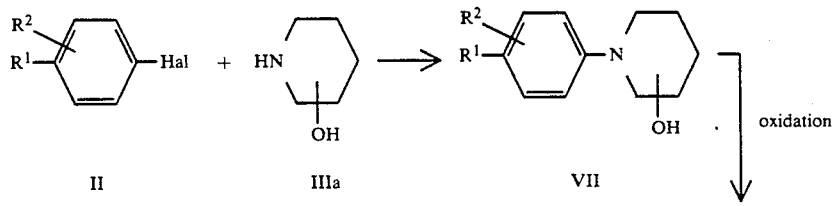

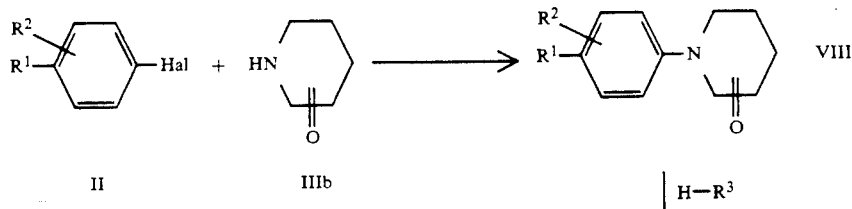

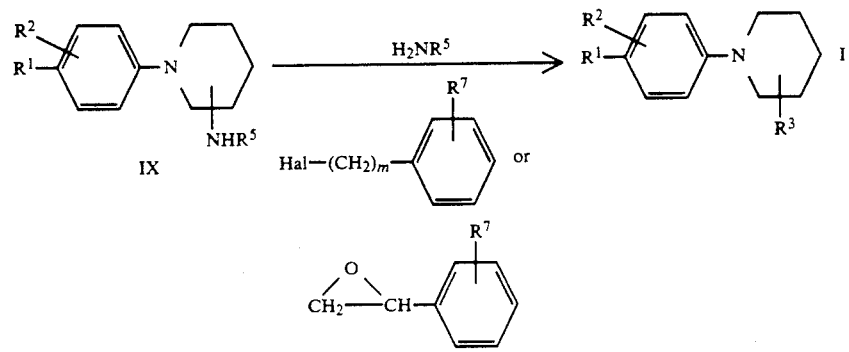

In process B) the halide II is reacted either under conditions similar to those in process A) initially with the piperidinol IIIa to give VII which is subsequently oxidized to VIII or with the piperidone IIIb directly to VIII. The alcohol VII is oxidized to the ketone VIII preferably by the method of Pfitzner-Moffat or Swern or by corresponding processes which are described in T. T. Tidwell, Synthesis (1990) 857.

The piperidone VIII is converted into the compounds I according to the invention by methods similar to those described in process A), by reductive amination either with the amine $R^3$-H or with $H_2NR^5$, and in the latter case the resulting amine is then alkylated with the halide

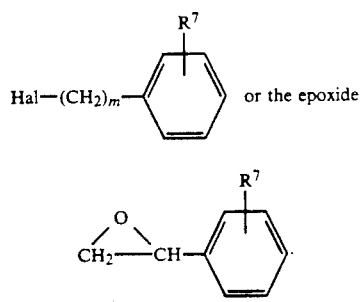

The statements concerning the pressure for process A) apply.

Process C)

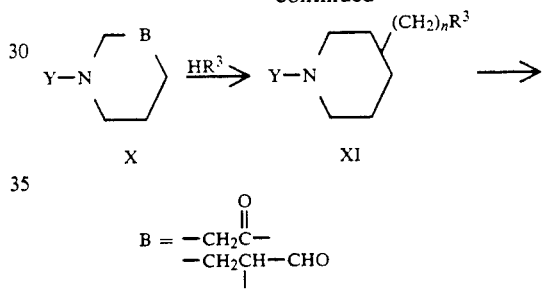

In a further variant, the compounds I are obtained in process C) by reacting the piperidine XII with the halide II under conditions similar to those for process A). Starting from the piperidine X where Y is a protective group such as benzyl, $CH_3$—CO—, $CF_3$—CO— or tert-butoxycarbonyl, reductive amination with the amine $HR^3$ under conditions similar to those for process A) results in the piperidine XI which is converted by elimination of the protective group Y into the piperidine XII. The protective group Y is eliminated in general either with hydrogen in the presence of catalysts such as Pd/carbon, Pt/carbon or Raney nickel, or by acidic or basic hydrolysis, e.g. with aqueous acids such as hydrochloric acid, sulfuric acid, or with bases, e.g. alkali metal hydroxides or carbonates such as NaOH, KOH, Na$_2$CO$_3$ and K$_2$CO$_3$. The reaction is expediently carried out at elevated temperatures, e.g. from 25° to 100° C. The statements concerning the pressure for process A) apply.

Process D)

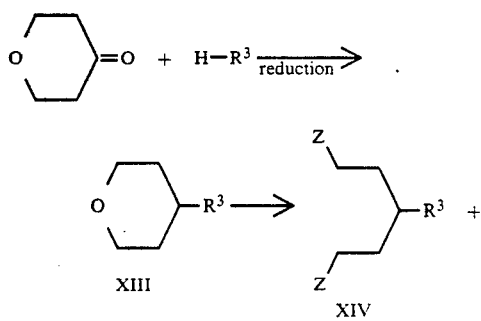

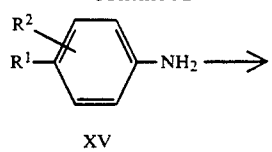

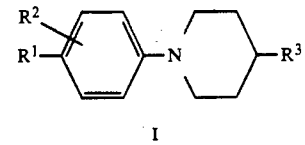

(Z = halogen, especially chlorine and bromine)

Another preparation route (process D)) starts from the tetrahydro-4-pyranone which is converted into XIII by reductive amination in a conventional manner, e.g. similar to the preparation of the compound I from VIII in process B). XIII is expediently converted into the dihalide XIV in a concentrated acid such as hydrobromic acid or hydrochloric acid, without solvent or in an inert solvent such as an alcohol, at elevated temperature, e.g. at from 50° to 100° C.

The subsequent alkylation of the aniline XV with XIV to give the compounds I according to the invention is expediently carried out in polar solvents such as alcohols and dimethylformamide or without solvent, in the presence or absence of a base such as NaOH and potassium carbonate. This reaction is generally carried out at from 50° to 150° C.

The statements concerning the pressure for process A) apply.

Process E)

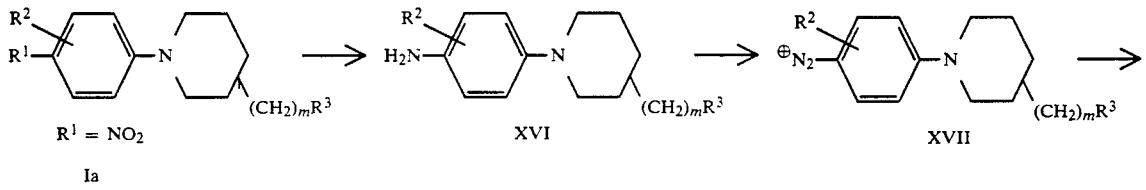

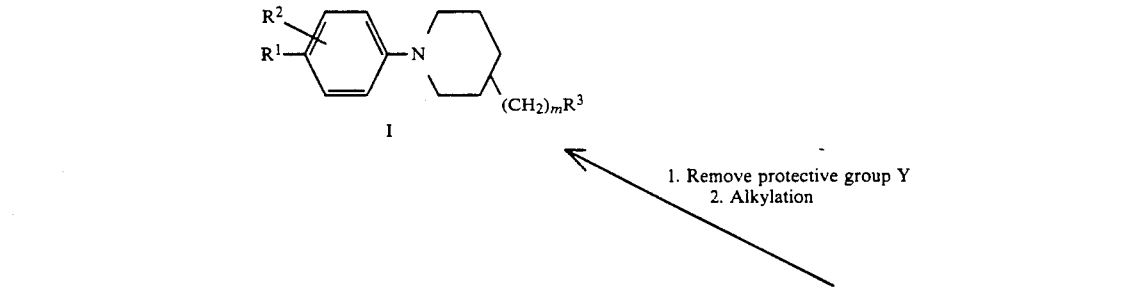

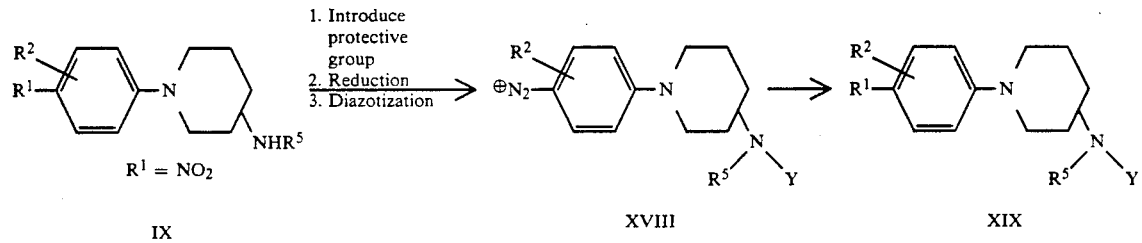

Y = Conventional protective group

In a first alternative of process E), synthetic routes starting from the nitro compounds Ia ($R^1=NO_2$) and IX ($R^1=NO_2$) allowing other substituents for $R^1$ to be introduced starting from the nitro group are depicted. To do this, the derivative Ia ($R^1=NO_2$) is reduced to the aniline XVI, either with hydrogen on hydrogenation catalysts such as Pd/carbon or Pt/carbon in, preferably, polar solvents such as alcohols, or with sodium borohydride/copper catalysis (Sung, Yoo et al., Synlett (1990) 419) or with reagents listed, for example, in Houben-Weyl, Methoden der organischen Chemie, Vol. 11/1, Chapter IV (such as Sn/HCl, Fe/HCl and $Na_2S_2O_4$). The aniline XVI is diazotized in a conventional manner (as described in Houben-Weyl, Methoden der organischen Chemie, Vol. 10/3, Chapter 1/A) and subsequently converted in a conventional manner (Houben-Weyl, Vol. 10/3, Chapter 1/B and literature cited therein) into other compounds I according to the invention which are different from Ia and in which $R^1$ is, for example, H, Cl and F.

In another alternative of process E), compound I is prepared starting from phenylpiperidine IX ($R^1=NO_2$). The conversion of the phenylpiperidine IX into I is carried out in several steps:
1. Introduction of a protective group Y for the secondary or primary amino group in IX, where Y is a conventional protective group such as $CH_3$—CO—, $CF_3$—CO— or tert-butoxycarbonyl, and is introduced in a conventional manner, e.g. as in process C),
2. Reduction of the nitro group,
3. Diazotization of the resulting aniline and
4. Conversion of the diazonium salt XVIII into XIX.

Stages 2 to 4 are carried out in a similar way to the first alternative of process E). The protective group Y in XIX is removed in conventional ways, e.g. in a similar manner to process C), and the resulting amine is alkylated with

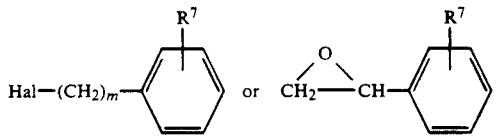

in a similar manner to process B) (conversion of IX into I).

The statements concerning the pressure for process A) apply.

The optical isomers are prepared in a conventional manner by formation of a salt of the racemic amine with optically active acids such as tartaric acid, dibenzoyltartaric acid, mandelic acid, ditolyltartaric acid or camphorsulfonic acid and subsequent separation by recrystallization (see P. Newman, Optical Resolution Procedures for Chemical Compouds, Vol. 1, New York, ca. 1979). The fractionation can take place either at the final stage, i.e. on the claimed amines I, or at an intermediate stage in processes A) to E), e.g. VI, IX and $HR^3$, in which case the subsequent reactions to give the final product I are carried out in a similar manner to the racemates but with only one antipode. The enantiomers are normally characterized either by measuring the specific rotation or by determining the enantiomer ratio by HPLC on chiral supports, or NMR with optically active shift reagents.

Physiologically tolerated acid addition salts can be prepared by reacting the substituted N-phenylpiperidines I in a conventional manner with conventional acids such as hydrochloric acid, hydrobromic acid, sulfuric acid, phosphoric acid, acetic acid, malonic acid, succinic acid, fumaric acid, maleic acid, citric acid, tartaric acid, lactic acid and oxalic acid [cf. Arzneimittelforschung 10 (1966) 224].

The compounds I can be administered orally, parenterally or intravenously in free form or, preferably, in the form of a salt with a physiologically tolerated acid (see above).

The dosage depends on the age, condition and weight of the patient and on the administration form. As a rule, the daily dose of active substance is from 0.01 to 25, preferably from 0.1 to 20, in particular from 1 to 10, mg/kg of body weight on oral administration, and from 0.5 to 5, preferably from 1 to 3, mg/kg of body weight on intravenous administration.

The compounds I can be administered in conventional solid or liquid pharmaceutical forms, e.g. uncoated or (film-)coated tablets, capsules, pills, powders, solutions or suspensions, infusion or injection solutions, and pastes, ointments, gels, creams, lotions, dusting powders, emulsions and sprays.

These are produced in a conventional manner. The active substances can for this purpose be processed with conventional pharmaceutical auxiliaries such as tablet binders, fillers, plasticizers, wetting agents, dispersants, emulsifiers, solvents, retarding agents and/or antioxidants (cf. H. Sucker et al., Pharmazeutische Technologie, Thieme Verlag Stuttgart 1978). The resulting formulations normally contain the active substance in an amount of from 0.1 to 99% by weight.

The compounds I are class III antiarrythmics (repolarization inhibitors). They also have affinity for the sigma receptor and therefore have an antipsychotic, anticonvulsant, anxiolytic and neuroprotective action.

EXAMPLES

A) Synthesis Examples

EXAMPLE 1

1-(4-Nitrophenyl)-4-[N-methyl-N-(4-nitrobenzyl-)aminomethyl]piperidine

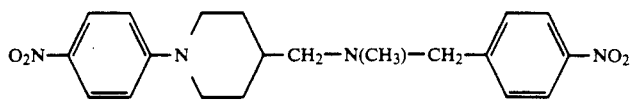

1.3 g of sodium cyanoborohydride were added a little at a time to a solution of 5.0 g (21.3 mmol) of 4-formyl-1-(4-nitrophenyl)piperidine, 3.5 g (21.3 mmol) of N,N-(4-nitrobenzyl)methylamine, 1.3 g of glacial acetic acid and 150 ml of methanol at about 20° C. After stirring for 16 hours, the solvent was removed under reduced pressure, and the residue was partitioned between water and ethyl acetate. The organic phase was worked up in a conventional way to give the product.

Yield: 7.3 g; melting point 162°–163° C.

Precursor 1.1

4-Diethoxymethyl-1-(4-nitrophenyl)piperidine

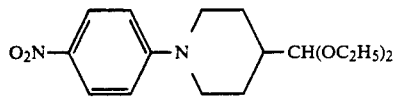

A mixture of 50.0 g (0.26 mol) of 4-diethoxymethylpiperidine, 37.3 g (0.26 mol) of 1-fluoro-4-nitrobenzene, 37.0 g (0.52 mol) of potassium carbonate and 500 ml of dimethylformamide was heated at 100° C. for 4 hours. The solvent was then removed under reduced pressure, and the residue was partitioned between water and ether acetate. The organic phase was then separated off, dried and concentrated.

Yield: 79.2 g; oil.

Analysis: calculated 62.3% C, 7.9% H, 9.1% N; found 62.3% C, 8.1% H, 9.6% N.

Precursor 1.2

4-Formyl-1-(4-nitrophenyl)piperidine

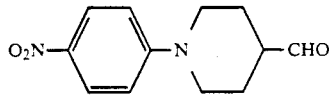

80.0 g (0.26 mol) of 4-diethoxymethyl-1-(4-nitrophenyl)piperidine in a mixture of 500 ml of water and 100 ml of concentrated aqueous hydrochloric acid were refluxed for 30 minutes. The solution was made alkaline with sodium hydroxide solution and then the product was extracted with diethyl ether. The product was then isolated in a conventional manner.

Yield: 90%; melting point 72°–73° C.

EXAMPLE 2

4-(N-Benzyl-N-methylaminomethyl)-1-(4-nitrophenyl)-piperidine

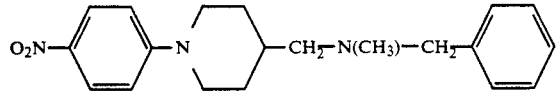

4.0 g (17.1 mmol) of 4-formyl-1-(4-nitrophenyl)piperidine, 2.1 g (17.1 mmol) of N-benzyl-N-methylamine, 1.0 g (17.1 mmol) of acetic acid and 1.1 g (17.1 mmol) of sodium cyanoborohydride were reacted as in Example 1.

Yield: 69%; melting point 91°–92° C.

EXAMPLE 3

N-[1-(4-Cyanophenyl)-4-piperidinyl]-N'-(4-nitrophenyl)piperazine

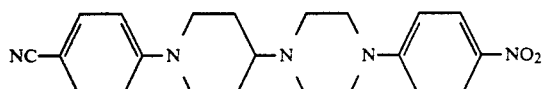

2.5 g of 1-(4-cyanophenyl)-4-piperidone [cf. Taylor et al., Synthesis (1981) 606] and 5.2 g of 1-(4-nitrophenyl)-piperazine were reacted as in Example 1.

Yield: 58%; melting point 243° C.

EXAMPLE 4

N-(4-Fluorophenyl)-N'-[1-(4-nitrophenyl)-4-piperidinyl]piperazine

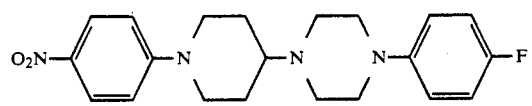

3.0 g (13.6 mmol) of 1-(4-nitrophenyl)-4-piperidone [cf. Taylor et al., Synthesis (1981) 606], 2.5 g (13.6 mmol) of N-(4-fluorophenyl)piperazine, 0.8 g (13.6 mmol) of acetic acid and 0.9 g (13.6 mmol) of sodium cyanoborohydride were reacted as in Example 1.

Yield: 62%; melting point: 191°–192° C.

EXAMPLE 5

4-(4-Chlorophenyl)-1-[1-(4-nitrophenyl)-4-piperidinyl]-4-piperidinol

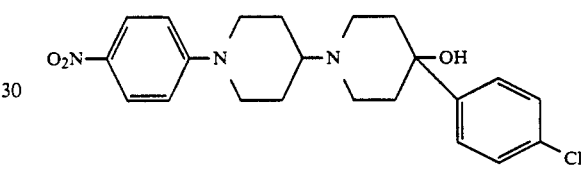

3.0 g (13.6 mmol) of 1-(4-nitrophenyl)-4-piperidone (cf. Taylor et al. Synthesis (1981) 606], 2.9 g (13.6 mmol) of 4-(4-chlorophenyl)-4-hydroxypiperidine, 0.8 g (13.6 mmol) of acetic acid and 0.9 g (13.6 mmol) of sodium cyanoborohydride were reacted as in Example 1.

Yield: 18%; melting point 225°–226° C.

EXAMPLE 6

2-[1-(4-Nitrophenyl)-4-piperidinyl]-1,2,3,4-tetrahydroisoquinoline

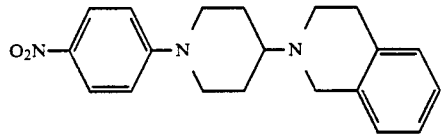

3.0 g of 1-(4-nitrophenyl)-4-piperidone and 1.8 g of 1,2,3,4-tetrahydroisoquinoline were reacted as in Example 1.

Yield: 74%; melting point 162°–163° C.

EXAMPLE 7

4-(4-Fluorophenyl)-1-[1-(4-nitrophenyl)-4-piperidinyl]-1,2,5,6-tetrahydropyridine

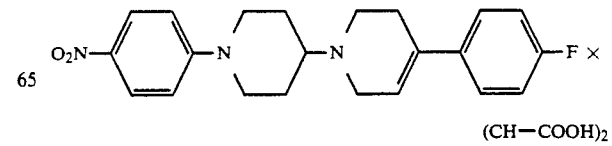

(CH—COOH)$_2$ 5.5 g of 1-(4-nitrophenyl)-4-piperidone and 4.4 g of 4-(4-fluorophenyl)-1,2,5,6-tetrahydropyridine were reacted as in Example 1. The product crystallized as fumarate.

Yield: 6.3g; melting point 182°-183° C.

EXAMPLE 8

1-(4-Nitrophenyl)-4-(4-phenyl-1-piperidinyl)piperidine

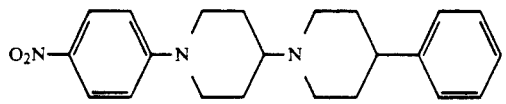

3.0 g of 1-(4-nitrophenyl) -4-piperidone and 2.2 g of 4-phenylpiperidine were reacted as in Example 1. The product contained 1/6 mol of water of crystallization.

Yield: 1.7 g; melting point 210°-211° C.

EXAMPLE 9

1-(4-Aminophenyl)-4-(4-phenyl-1-piperidinyl)piperidine

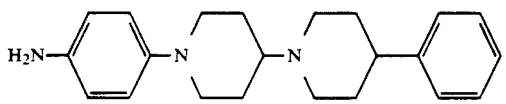

0.5 g of palladium carbon (containing 10% by weight palladium) was added to a solution of 1.2 g (2.7 mmol) of 1-(4-nitrophenyl)-4-(4-phenyl-1-piperidinyl)piperidine (cf. Example 8) in 100 ml of methanol. Hydrogenation was continued until hydrogen uptake ceased, then the solids were filtered off and the solvent was removed under reduced pressure.

Yield: 92%; melting point 156°-157° C.

EXAMPLE 10

1-(4-Methanesulfonamidophenyl)-4-[N-(4-methanesulfonamidobenzyl)-N-methylaminomethyl]piperidine

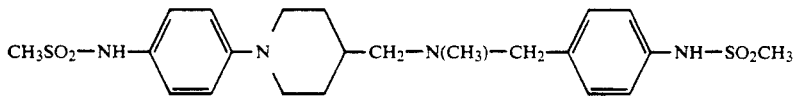

To a suspension of 5.4 g (14.0 mmol) of the base from 1-(4-nitrophenyl)-4-[N-methyl-N-(4-nitrobenzyl)aminomethyl]piperidine fumarate in 150 ml of ethanol were added, at 20° to 25° C., a solution of 0.8 g (3.2 mmol) of copper sulfate pentahydrate in 2 ml of water and then 5.3 g (140 mmol) of sodium cyanoborohydride. The mixture was refluxed for 3 hours, then the resulting solid was separated off, and the solvent was removed under reduced pressure. The residue was partitioned between water and ethyl acetate, after which the organic phase was separated off and concentrated under reduced pressure.

A solution of 2.8 g (12.3 mmol) of methanesulfonyl chloride in 30 ml of anhydrous tetrahydrofuran was added dropwise to a solution of 4.0 g (12.3 mmol) of the 1-(4-aminophenyl)-4-[N-methyl-N-(4-aminobenzyl)aminomethyl]piperidine prepared in this way and 10.0 g (98.6 mmol) of triethylamine in 350 ml of anhydrous tetrahydrofuran at 0° C. The mixture was then stirred at 0° C. for 2 hours and subsequently diluted with 200 ml of saturated aqueous sodium bicarbonate solution. The solvent was removed under reduced pressure and then the residue was extracted with methylene chloride. The organic phase was dried and concentrated. The crude product was purified by chromatography on silica gel (mobile phase: methylene chloride/methanol 10:1).

Yield: 1.6 g;

Analysis $(C_{22}H_{32}N_4S_2O_4 \times 0.5\ H_2O)$: calculated 54.0% C, 6.8% H, 11.4% N, 13.1% S; found 54.1% C, 6.8% H, 11.3% N, 12.8% S.

EXAMPLE 11

3-(N-benzyl-N-methylamino)-1-(4-nitrophenyl)piperidine

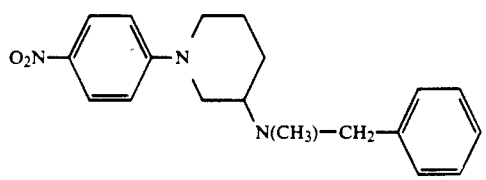

2.5 g (11.4 mmol) of 1-(4-nitrophenyl)-3-piperidone were reacted with 1.4 g (11.4 mmol) of N-benzyl-N-methylamine as in Example 1.

Yield: 20%; melting point 107°-108° C.

Precursor 11.1

3-Hydroxy-1-(4-nitrophenyl)piperidine

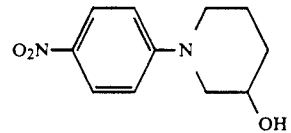

A mixture of 21.5 g (0.21 mmol) of 3-hydroxypiperidine, 30.0 g (0.21 mmol) of 4-fluoro-1-nitrobenzene, 30.0 g (0.22 mmol) of potassium carbonate and 250 ml of dimethylformamide was heated at 100° C. for 4 hours and then worked up as for precursor 1.1. The oily crude product was crystallized from methanol.

Yield: 71%; melting point 126° C.

Precursor 11.2

1-(4-Nitrophenyl)3-piperidone

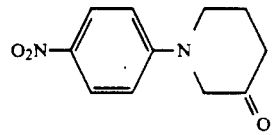

20.0 g (90 mmol) of 3-hydroxy-1-(4-nitrophenyl)piperidine, 7.1 g (90 mmol) of pyridine and 56.0 g (270 mmol) of dicyclohexylcarbodiimide were dissolved in a mixture of 100 ml of anhydrous dimethyl sulfoxide and 200 ml of anhydrous toluene. The solution was cooled to 0° C. and then 3.4 ml (45 mmol) of trifluoroacetic acid were added dropwise, after which the resulting mixture was stirred at about 20° C. for 16 hours and subsequently diluted with water. The organic phase was separated off and worked up to the product as usual.

Yield: 78%; melting point 127°-129° C.

EXAMPLE 12

4-[N-[2-(4-Fluorophenyl)-2-hydroxyethyl]-N-methylamino]-1-(4-nitrophenyl)piperidine

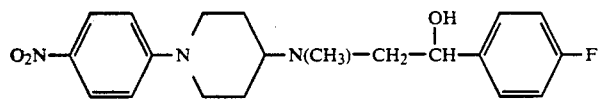

A mixture of 3.0 g (12.8 mmol) of 4-methylamino-1-(4-nitrophenyl)piperidine fumarate, 1.8 g (12.8 mmol) of 4-fluorostyrene oxide and 100 ml of ethanol was refluxed for 3 hours. The solvent was then removed under reduced pressure, and the residue was partitioned between ethyl acetate and water. The organic phase was separated off, dried and concentrated under reduced pressure. Purification was by chromatography on silica gel (mobile phase: methylene chloride/methanol 10:1).

Yield: 14%; melting point 91°-92° C.

Precursor 12.1

4-Methylamino-1-(4-nitrophenyl)piperidine fumarate

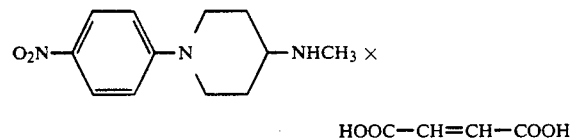

15.0 g (68 mmol) of 1-(4-nitrophenyl)-3-piperidone (cf. E. Taylor et al., Synthesis (1981) 606] and then 4.3 g (68 mmol) of sodium cyanoborohydride were added a little at a time to a methylamine-saturated solution of 43 ml of acetic acid in 400 ml of methanol. The mixture was stirred at about 20° C. for 16 hours and then the solvent was removed under reduced pressure and the residue was partitioned between methylene chloride and water. The organic phase was worked up to the product as usual. The product was crystallized as the fumarate.

Yield: 73%; melting point 189°-190° C.

EXAMPLE 13

4-[N-[2-Hydroxy-2-(4-nitrophenyl)ethyl-N-methylamino]-1-(4-nitrophenyl)piperidine

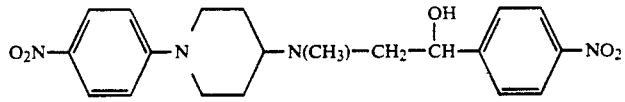

A mixture of 3.0 g (12.8 mmol) of 4-methylamino-1-(4-nitrophenyl)piperidine, 2.6 g (25.5 mmol) of triethylamine, 3.1 g (12.8 mmol) of 2-bromo-1-(4-nitrophenyl)ethanol and 150 ml of methanol was stirred at 20° C. for 1 hour. The mixture was then partitioned between saturated aqueous potassium carbonate solution and methylene chloride. The organic phase was then separated off, dried and concentrated under reduced pressure. The crude product was purified by chromatography on silica gel (mobile phase: toluene/acetone 1:1).

Yield: 85%.

Analysis $C_{20}H_{24}N_4O_5$: calculated 60.0% C, 6.0% H, 14.0% N; found 60.1% C, 6.1% H, 13.9% N.

EXAMPLE 14

4-[N-[2-Hydroxy-2-(4-methanesulfonamidophenyl)ethyl]-N-methylamino]-1-(4-methanesulfonamidophenyl)piperidine

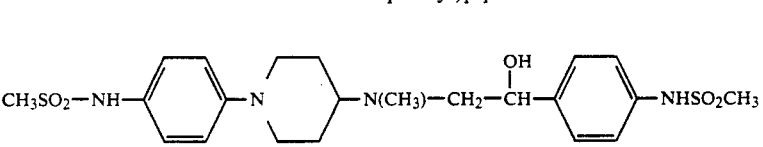

0.5 g of palladium/carbon (containing 10% by weight palladium) was added to a solution of 4.0 g (10.0 mmol) of 4-[N-[2-hydroxy-2-(4-nitrophenyl)ethyl]-N-methylamino]-1-(4-nitrophenyl)piperidine in 200 ml of methanol. Hydrogenation was continued until hydrogen uptake ceased, then the solids were filtered off and the solvent was removed under reduced pressure. The resulting dianiline derivative was reacted with methanesulfonyl chloride as in Example 10.

Yield: 0.45 g;

$^1$H-NMR (in D6-DMSO; TMS as internal standard): 1.5 ppm (2H), 1.7 ppm (2H), 2.3 ppm (2H), 2.5 ppm (3H), 2.6 ppm (1H), 2.9 ppm (3H), 3.0 ppm (3H), 3.2 ppm (2H), 3.7 ppm (2H), 4.1 ppm (1H), 4.6 ppm (1H), 6.9 ppm (2H), 7.05 ppm (2H), 7.1 ppm (2H), 7.3 ppm (2H), 9.2 ppm (1H) and 9.7 ppm (1H).

EXAMPLE 15

1-(4-Chlorophenyl)-4-[N-[2-(4-fluorophenyl)-2-hydroxyethyl]-N-methylamino)piperidine dioxalate

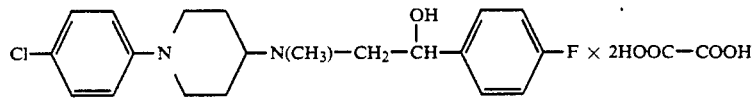

A mixture of 2.0 g (8.9 mmol) of 1-(4-chlorophenyl)-4-methylaminopiperidine, 1.2 g (8.9 mmol) of 4-fluorostyrene oxide and 100 ml of ethanol was refluxed for 5 hours. The solvent was then removed, after which the crude product was purified by chromatography on silica gel (mobile phase toluene/acetone 1:1). The product crystallized as dioxalate.

Yield: 2.3 g; melting point 91°–92° C.

Precursor 15.1

4-(N-Methyl-N-trifluoroacetylamino)-1-(4-nitrophenyl)piperidine

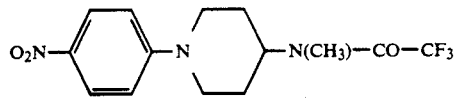

2.4 g (30.6 mmol) of pyridine were added to a solution of 3.6 g (15.3 mmol) of 4-methylamino-1-(4-nitrophenyl)piperidine fumarate (cf. precursor 12.1) in 50 ml of anhydrous tetrahydrofuran. A solution of 3.5 g (16.8 mmol) of trifluoroacetic anhydride in 10 ml of anhydrous tetrahydrofuran was then added dropwise to the mixture at 0° C. After stirring at 20° to 25° C. for 72 hours, the solvent was removed under reduced pressure and the residue was partitioned between water and methylene chloride. The organic phase was then worked up to the product as usual.

Yield: 87%; melting point 104°–105° C.

Precursor 15.2

1-(4-Aminophenyl)-4-(N-methyl-N-trifluoroacetylamino)piperidine

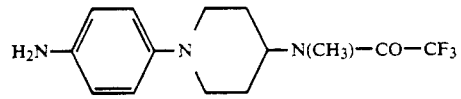

A solution of 3.8 g (11.5 mmol) of 4-(N-methyl-N-trifluoroacetylamino)-1-(4-nitrophenyl)piperidine in 100 ml of methanol was hydrogenated on a palladium/carbon catalyst (10% by weight palladium). After hydrogen uptake ceased, the solids were removed from the mixture by filtration, after which the solvent was removed under reduced pressure.

Yield: 96%; melting point 120°–121° C.

Precursor 15.3

1-(4-Chlorophenyl)-4-methylaminopiperidine

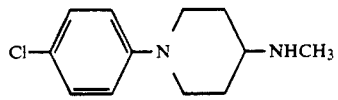

Solution A

A solution of 0.7 g of sodium sulfite in 2.2 ml of water was added to a solution of 2.7 g of copper(II) sulfate×5 H₂O and 1.0 g of sodium chloride in 8.8 ml of water. Resulting solids were separated off and dissolved in concentrated hydrochloric acid, after which the two solutions were combined.

To a solution of 3.3 g (10.9 mmol) of 1-(4-aminophenyl)-4-(N-methyl-N-trifluoroacetylamino)piperidine in 3.7 ml of 32% by weight hydrochloric acid were successively added 2 ml of water and, at 0° C. dropwise, a solution of 0.76 g of sodium nitrite in 4.4 ml of water.

Solution A was rapidly added and then the mixture was heated on a water bath until gas evolution ceased and then poured into ice, and concentrated aqueous ammonia solution was added. The product was then extracted with methylene chloride and isolated as usual.

Yield: 96%; melting point 44°–46° C.

EXAMPLE 16

1-(4-Chlorophenyl)-4-(4-phenyl-1-piperidinyl)piperidine

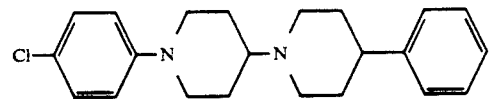

1.0 g (3 mmol) of 1-(4-aminophenyl)-4-(4-phenyl-1-piperidinyl)piperidine (cf. Example 9) was diazotized and then converted into the chlorine derivative as for precursor 15.3.

Yield: 72%; melting point 173° C.

B) Antiarrythmic Effect

The effect of the phenylpiperidines I as repolarization inhibitors can be demonstrated by ECG measurements. In this connection, the cardiac cycle is divided into systole (contraction of the heart), also called QT interval, and diastole (relaxation of the heart with filling of the ventricles with blood). Repolarization inhibitors increase the QT interval but have a negligible effect on the atrioventricular conduction time (PQ interval) and the period of isometric contraction (QRS time, from start of systole to opening of the semilunar valves) (see Pschyrembel, 254th Edition, 1982).

The activity of the compounds according to the invention as repolarization inhibitors can be investigated in animal experiments by ECG measurements on, for example, guinea-pig hearts (see Basic Res. Cardiol. 82 (1987) 437; J. Pharmacol. Methods 21 (1989) 195). Comparison of the activities of various substances is based, for example, on the dose of an active substance at which the QT interval is increased by 20% from the initial level ($ED_{20\%}$). To do this, the logarithms of the doses of the substances are plotted against the experimentally found relative changes in the QT interval, and linear regression is used to determine the equation of a straight line from which the $ED_{20\%}$ can then be calculated.

This method was used to determine the $ED_{20\%}$ values of compounds according to the invention (see Table 1). The comparison substance was D-sotalol [4'-(1-hydroxy-2-(isopropylamino)ethyl)methanesulfonanilide].

The experimental animals were male Duncin-Hartley guinea-pigs weighing from 300 to 350 g. 30 min after administration of 1250 I.U. of heparin/kg of body weight into the abdominal cavity, the animals were sacrificed by a blow to the back of the neck. The common carotid arteries were severed for exsanguination, then the thoracic cavity was opened and the heart was removed and connected to a perfusion apparatus. The Langendorff perfusion was carried out with oxygen-enriched Krebs-Henseleit solution (NaCl 6896 mg/l; KCl 350 mg/l; MgSO₄ 285 mg/l; CaCl₂ 370 mg/l; KH₂PO₄ 161 mg/l; NaHCO₃ 2090 mg/l; glucose 2000 mg/l) at 37° C. The perfusion volume per unit time was 4 to 6 ml/min, the total volume was 100 ml and the perfusion pressure was 60 to 70 mm Hg. Circulating perfusion was carried out after an equilibration time of 30 min.

Two silver electrodes attached to the surface of the heart in the upper region of the left coronary artery and on the rear of the heart at the level of the valve were used for the ECG recordings. The PQ and QT intervals and QRS times, and the heart rate, were measured.

The substances were added to the perfusate cumulatively at 15 min intervals.

TABLE 1

QT-prolonging effect of substituted N-phenylpiperidines I compared with D-sotalol.

| Example No. | $ED_{20\%}$ [μmol/l] |
| --- | --- |
| 2 | 0.42 |
| 3 | 0.031 |
| 10 | 0.96 |
| 11 | 1.1 |
| 12 | 0.21 |
| D-sotalol | 16.0 |

C) Sigma Receptor Binding

The binding assay used (binding of [$^3$H]-ditolylguanidine) involves haloperidol-sensitive sigma receptors which have a high affinity for haloperidol but only low affinity for phencyclidine and opioids.

1,3-Di-o-tolylguanidine (DTG), the selective ligand for this binding site [cf. Life Sciences 47 (1990) 1073], was used as reference substance. Methods:

a) Membrane Preparation

Rat cerebra were homogenized in 10 times the volume of homogenization buffer (50 mmol/l tris(hydroxymethyl)aminomethane, 0.1 mmol/l ethylenediaminetetraacetate, pH=7.7) with a Polytron homogenizer (20 sec.). The pellet obtained after centrifugation at 40 000 rpm for 15 minutes was resuspended and the suspension was again centrifuged at 40 000 rpm for 15 minutes. The resulting pellet was resuspended in 5 times the volume of homogenization buffer and stored in liquid nitrogen until used.

Sigma Binding Assay

Test substance and membranes (0.3 mg of protein) were incubated in 0.3 ml of incubation buffer (5 mmol/l tris(hydroxymethyl)aminomethane, 0.1 mmol/l ethylenediaminetetraacetate, pH=7.7) at 37° C. for 45 minutes. 100 000 dpm of [$^3$H]-ditolylguanidine (54.5 Ci/mmol) were added and the mixture was then incubated for 1 hour. The membranes were filtered through GF/B filters (dunn-Labortechnik, Asbach) and washed with washing buffer (5 mmol/l tris (hydroxymethyl) aminomethane, 0.1 mmol/l ethylenediaminetetraacetate, pH=7.4) at 37° C. The radioactivity remaining on the filters was measured by liquid scintillation counting. The binding data were analyzed by iterative fitting programs.

The activity constants $K_i$ of substituted N-phenylpiperidines I are to be found in Table 2.

TABLE 2

Activity constants $K_i$ for the [$^3$H]-ditolylguanidine binding site

| Example No. | $K_i$ [nM] |
| --- | --- |
| 2 | 11 |
| 8 | 2.8 |
| 11 | 2.0 |
| DTG | 29.1 |

We claim:

1. A substituted N-phenylpiperidine of the formula I

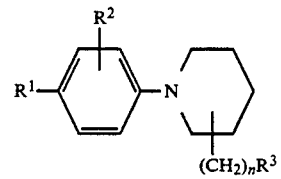

where
$R^1$ is hydrogen, nitro, cyano, halogen, $C_1$-$C_4$-alkyl, trifluoromethyl, trifluoromethoxy, hydroxyl, hydroxymethyl, hydroxycarbonyl, formyl, formylamino, amino, aminocarbonyl, 5-tetrazinyl, $R^4$—O—, $R^4$—O—$CH_2$—, $R^4$—O—CO—, $R^4$—CO—, $R^4$—NH—CO, $R^4$—CO—NH—, $R^4$—$SO_2$—NH—;
$R^2$ is hydrogen, nitro, halogen, $C_1$-$C_4$-alkyl or $R^4$—O—;
$R^3$ is one of the following:

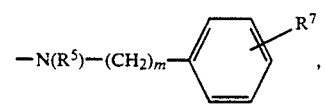

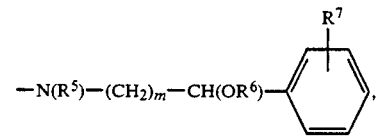

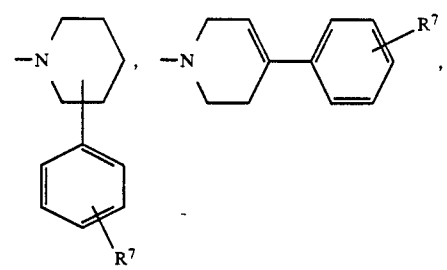

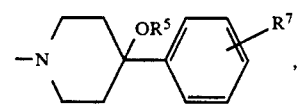

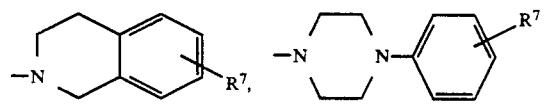

$R^4$ is $C_1$-$C_4$-alkyl or phenyl which may carry one of the $R^2$ radicals;
$R^5$ and $R^6$ are each hydrogen, $C_1$-$C_4$-alkyl or phenyl which can carry one of the $R^2$ radicals;

$R^7$ is one of the $R^1$ radicals n is 0 or 1;

m is 1 or 2; with the proviso that $R^3$ can be

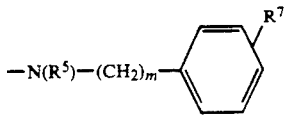

only when n is 1, and the optical isomers when there is optical isomerism, and the physiologically tolerated acid addition salts.

2. A pharmaceutical composition which contains as the active substance, 0.1 to 90% by weight of a substituted N-phenylpiperidine of the formula I as claimed in claim 1.

3. An antiarrythmic composition containing conventional auxiliaries and a therapeutically effective amount of an N-phenylpiperidine of the formula I as claimed in claim 1.

* * * * *